United States Patent
Xue et al.

(10) Patent No.: US 12,063,930 B2
(45) Date of Patent: Aug. 20, 2024

(54) SULFONAMIDE-CONTAINING 4-(N-METHYL) AMINOPIPERIDINE MYRICETIN DERIVATIVES, PREPARATION METHOD AND APPLICATION

(71) Applicant: Guizhou University, Guiyang (CN)

(72) Inventors: Wei Xue, Guiyang (CN); Shichun Jiang, Guiyang (CN); Ying Chen, Guiyang (CN); Shijun Su, Guiyang (CN); Jun He, Guiyang (CN); Mei Chen, Guiyang (CN); Meimei Jin, Guiyang (CN); Ming He, Guiyang (CN); Jun Wang, Guiyang (CN)

(73) Assignee: Guizhou University, Guiyan (CN)

( * ) Notice: Subject to any disclaimer, the term of this patent is extended or adjusted under 35 U.S.C. 154(b) by 207 days.

(21) Appl. No.: 17/043,521

(22) PCT Filed: Dec. 9, 2019

(86) PCT No.: PCT/CN2019/124090
§ 371 (c)(1),
(2) Date: Sep. 29, 2020

(87) PCT Pub. No.: WO2020/253152
PCT Pub. Date: Dec. 24, 2020

(65) Prior Publication Data
US 2023/0131193 A1    Apr. 27, 2023

(30) Foreign Application Priority Data
Jun. 18, 2019  (CN) .......................... 201910528656.3

(51) Int. Cl.
| | | |
|---|---|---|
| *A61K 31/277* | (2006.01) | |
| *A01N 43/40* | (2006.01) | |
| *A01P 1/00* | (2006.01) | |
| *C07D 405/12* | (2006.01) | |

(52) U.S. Cl.
CPC ................ *A01N 43/40* (2013.01); *A01P 1/00* (2021.08); *C07D 405/12* (2013.01)

(58) Field of Classification Search
None
See application file for complete search history.

(56) References Cited

FOREIGN PATENT DOCUMENTS

| | | |
|---|---|---|
| CN | 104788416 | 7/2015 |
| CN | 106518828 | 3/2017 |
| CN | 109438433 | 8/2019 |
| CN | 110183430 | 8/2019 |

OTHER PUBLICATIONS

Jiang, Shichun, Design, Synthesis and Antibacterial Activities Against Xanthomonas *Oryzae* pv.*Oryzae*, Xanthomonas *Axonpodis* pv.*Citri* and Ralstonia Solanacearum of Novel Myricetin Derivatives Containing Sulfonamide Moiety, Pest Manag Sci. Sep. 5, 2019.

*Primary Examiner* — Layla Soroush

(57) ABSTRACT

The invention discloses a 4-(N-methyl) aminopiperidine myricetin derivatives containing sulfonamide, a preparation method and application, whose structural general formula is shown as follows: Wherein, R is substituted phenyl and substituted aromatic heterocyclic group; n is the number of carbon in the carbon chain and is 2, 3, 4 and 5 respectively. The substituted phenyl group is an alkyl group containing C1-6, an alkoxy group containing C1-6, a nitro group, a halogen atom or a hydrogen atom in ortho, meta and para positions on the benzene ring. The substituted aromatic heterocyclic group is thienyl, furyl, pyrrolyl, pyridyl, etc., and the substituent on the aromatic heterocyclic ring is an alkyl group containing C1-6, alkoxy group of C1-6, nitro group, halogen atom or hydrogen atom in ortho, meta and para positions. The invention has a better control effect on inhibiting plant germs and can be used as an agricultural bactericide.

1 Claim, No Drawings

SULFONAMIDE-CONTAINING 4-(N-METHYL) AMINOPIPERIDINE MYRICETIN DERIVATIVES, PREPARATION METHOD AND APPLICATION

FIELD OF THE INVENTION

The invention relates to the technical field of chemical industry, in particular to a 4-(N-methyl) aminopiperidine myricetin derivatives containing sulfonamide, a preparation method of the 4-(N-methyl) aminopiperidine myricetin derivatives containing sulfonamide, and application of the 4-(N-methyl) aminopiperidine myricetin derivatives containing sulfonamide in inhibiting plant pathogens.

BACKGROUND OF THE INVENTION

Myricetin (3',4',5',3,5,7-hexahydroxyflavonol, also known as Cannabiscetin and Myricetol, is a polyhydroxyflavone compound separated from myricetin bark, chemical formula C15 H10 O8, relative molecular weight 318.24, yellow needle-like or granular crystal, melting point 324-326° C., soluble in methanol, ethanol and acetone, insoluble in chloroform and petroleum ether. It exists in Fagaceae, leguminosae, primulaceae, vitaceae, compositae and other plants. According to modern pharmacological activity research. Myricetin has a variety of pharmacological activities such as bacteriostasis, antiallergic, antiviral, hypoglycemic, anti-inflammatory, antioxidant, nerve protection and so on, showing rich resource advantages and great potential utilization value.

In 2007, Naz et al. (Journal of Food Science and Technology, 2007, 72, 341-345) studied the in vitro antibacterial activity of Myricetin against 4 genera of *Staphylococcus, Corynebacterium, Streptococcus* and *Bacillus subtilis*. The results showed that Myricetin had different degrees of antibacterial effect on the above 4 genera.

In 2009, Liu et al. (Journal of Zhejiang A&F University, 2009, 26, 95-99) conducted a systematic bacteriostasis action test on Myricetin by growth rate method. The experimental results showed that Myricetin had strong inhibitory activity on 6 plant pathogenic fungi including rice sheath blight fungus, *Sclerotinia sclerotiorum*, tomato *Botrytis cinerea*, wheat scab fungus, apple rot fungus, cotton *Fusarium* wilt, etc. The EC50 were: 0.32, 0.33, 1.09, 0.69, 0.34 and 2.09 g/L, and have higher inhibitory activity on rice sheath blight, rape *Sclerotinia sclerotiorum* and apple rot.

In 2012, Yu et al. (bioorganic chemistry and Pharmacochemistry Express, 2012, 22, 4049-4054) studied the inhibitory effect of Myricetin on SARS virus in vitro by performing fluorescence resonance energy transfer (FRET) double-stranded DNA derotation assay or using colorimetric basic hydrolysis assay. The study found that: Myricetin potentially inhibits SARS virus helicase protein and affects ATP enzyme activity, but has no helicase activity, and Myricetin has no cytotoxicity on normal breast epithelial MCF10A cells. Furthermore, Myricetin has a good inhibitory effect on SARS virus in vitro.

To sum up, Myricetin has certain biological activity in medicine and pesticide. Previous research work has less modification on Myricetin, mainly research on the biological activity of Myricetin itself, but there has been no report of introducing the active group of 4-(N-methyl) aminopiperidine containing sulfonamide into Myricetin to synthesize 4-(N-methyl) aminopiperidine myricetin derivatives containing sulfonamide and carrying out agricultural activity test.

SUMMARY OF THE INVENTION

The object of the present invention is to provide a 4-(N-methyl) aminopiperidine myricetin derivatives containing sulfonamide, which overcomes the above disadvantages and has a good control effect on plant pathogenic fungi, and can be used as an agricultural fungicide.

Another object of the present invention is to provide a preparation method of the sulfonamide-containing 4-(N-methyl) aminopiperidine myricetin derivatives.

Another object of the invention is to provide the application of the sulfonamide-containing 4-(N-methyl) aminopiperidine myricetin derivatives in inhibiting citrus canker germs and rice bacterial leaf blight germs.

The 4-(N-methyl) aminopiperidine myricetin derivatives containing sulfonamide of the invention has the following structural general formula:

$$n = 2, 3, 4, 5 \quad \text{(I)}$$

Wherein, R is substituted phenyl or substituted aromatic heterocyclic group; n is the number of carbon in the carbon chain and is 2, 3, 4 and 5 respectively.

The sulfonamide-containing 4-(N-methyl) aminopiperidine myricetin derivatives, wherein: The substituted phenyl group is a C1-6 alkyl group, a C1-6 alkoxy group, a nitro group, a halogen atom and a hydrogen atom in the ortho, meta and para position on the benzene ring.

The above-mentioned 4-(N-methyl) aminopiperidine myricetin derivatives containing sulfonamide, wherein: Substituted aromatic heterocyclic groups are thienophenyl, furyl, pyrrolyl, pyridyl and the like, and substituents on the substituted aromatic heterocyclic groups are ortho, meta and para position alkyl groups containing C1-6, C1-6 alkoxy groups, nitro groups, halogen atoms and hydrogen atoms.

The preparation method of the sulfonamide-containing 4-(N-methyl) aminopiperidine myricetin derivatives of the invention has the following synthetic route:

(1) 3-hydroxy-3',4',5',5,7-pentamethoxy myricetin (intermediate a) is prepared from myricetin and methyl iodide as raw materials and crystalline potassium carbonate as catalyst through acidic adjustment.

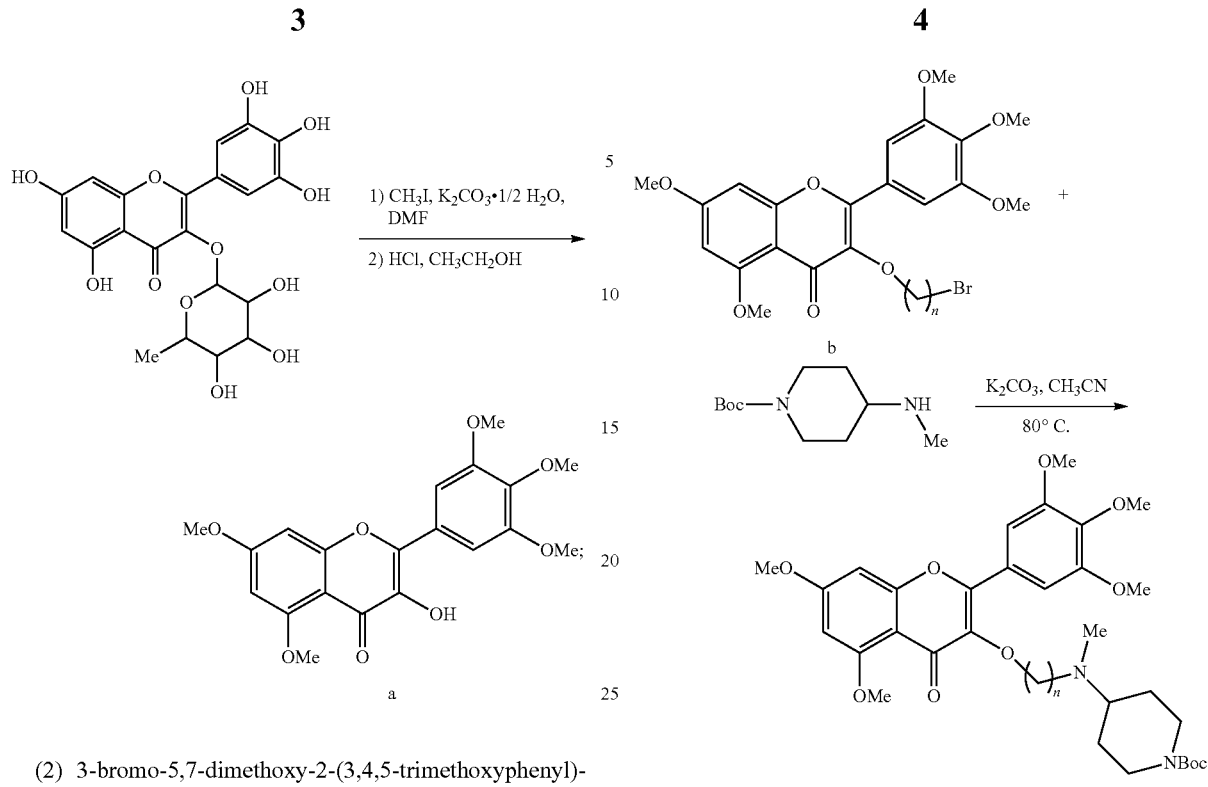

(2) 3-bromo-5,7-dimethoxy-2-(3,4,5-trimethoxyphenyl)-4H-chromene-4-one (intermediate b) is prepared from intermediate a and dibromoalkanes with different chain lengths as raw materials, potassium carbonate as catalyst and N, N-dimethylformamide (DMF) as solvent, as shown below:

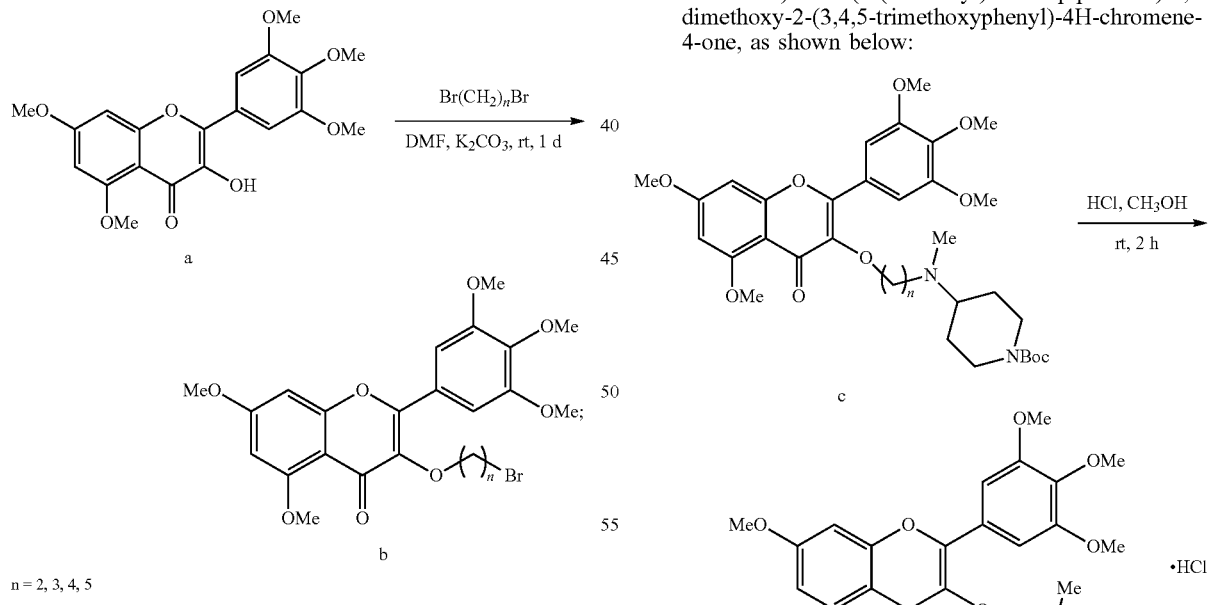

n = 2, 3, 4, 5

(3) Using intermediate b and 4-(N-methyl) amino-N-Boc piperidine as raw materials, potassium carbonate as catalyst and acetonitrile as solvent, 3-(4-(N-methyl) amino-N-Boc piperidine)-5,7-dimethoxy-2-(3,4,5-trimethoxyphenyl)-4H-chromene-4-one (intermediate c) is prepared under reflux and stirring at 80° C., as shown below:

n = 2, 3, 4, 5

(4) Taking intermediate c as a raw material, Boc protection is removed by HCl to obtain hydrochloride (intermediate d) of 3-(4-(N-methyl) aminopiperidine)-5,7-dimethoxy-2-(3,4,5-trimethoxyphenyl)-4H-chromene-4-one, as shown below:

n = 2, 3, 4, 5

(5) Intermediate d and substituted sulfonyl chloride are used as raw materials, potassium carbonate is used as a catalyst, and absolute ethyl alcohol is used as a solvent to prepare 4-(N-methyl) aminopiperidine myricetin derivatives containing sulfonamides (target compound I), as shown below.

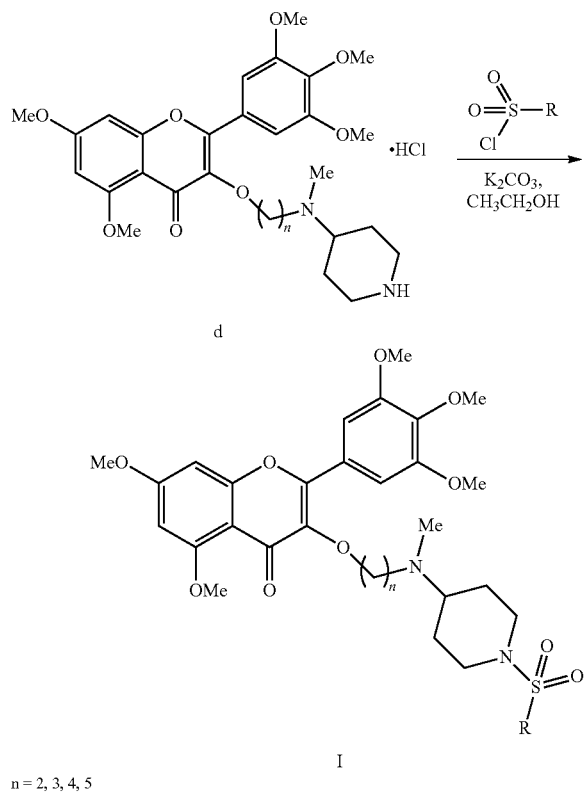

n = 2, 3, 4, 5

The application of the sulfonamide-containing 4-(N-methyl) aminopiperidine myricetin derivatives of the invention in inhibiting citrus canker germs and rice bacterial leaf blight germs.

Compared with the prior art, the invention has obvious beneficial effects, and can be seen from the above technical scheme: In the synthesis of intermediate a of the invention, crystalline potassium carbonate is cheaper than anhydrous potassium carbonate, and the yield is improved. In the invention, piperidine, an alkaloid structural unit, is mainly used as a bridge, and natural products myricetin and sulfonyl chloride are actively spliced, so that the obtained compound has higher bacteriostatic activity.

DETAILED DESCRIPTION OF THE INVENTION

Embodiment 1

The preparation method of 5,7-dimethoxy-3-(3-(N-methyl (1-(4-methylbenzenesulfonyl) piperidyl)) amino) propoxy)-2-(3,4,5-trimethoxyphenyl)-4H-chromene-4-one (target compound I1) is as follows:

(1) Preparation of 3-hydroxy-3',4',5',5,7-pentamethoxy myricetin (Intermediate a)

4.64 g of Myricetin (10 mmol), 22.09 g K2CO3 (160 mmol) and 120 mL DMF are sequentially added into a 250 mL round bottom flask. After stirring at normal temperature for 0.5 to 1 h, 7.50 mL of methyl iodide (120 mmol) is slowly added dropwise, stirring at room temperature for 48 h, and monitoring the reaction by TLC (methanol:ethyl acetate=1:4, V/V). After the reaction is stopped, the precipitate is filtered and the filter residue is washed with dichloromethane, then the combined filtrates are, diluted with 100 mL of water, extracted three times with dichloromethane, the organic layers are combined, concentrated under reduced pressure, then the concentrate is dissolved in 30 mL of absolute ethyl alcohol to heat to reflux, after the solution is clarified, 10 mL of concentrated hydrochloric acid is added under reflux, then yellow solid is precipitated, the reaction is continued for 2 hours, cooled, filtered, and the crude product 3-hydroxy-3',4',5',5,7-pentamethoxy myricetin (intermediate a) is obtained with a 54.4% yield.

(2) Preparation of 3-(3-bromopropoxy)-5,7-dimethoxy-2-(3,4,5-trimethoxyphenyl)-4H-chromene-4-one (Intermediate b)

1.17 g (3 mmol) of 3-hydroxy-3',4',5',5,7-pentamethoxy myricetin (intermediate a), 1.66 g of K2CO3 (12 mmol) and 30 mL DMF are sequentially added into a 100 mL single-necked round bottom flask. After stirring at normal temperature for 0.5-1 h, 2.42 g of 1,3-dibromopropane (12 mmol) are added. The reaction is continued for 12 hours at this temperature, and the reaction (ethyl acetate) is monitored by TLC. After the reaction is stopped, the reaction solution is dispersed with 50 mL of water and extracted with ethyl acetate (3×25 ml). The obtained ethyl acetate layer is washed with 1 mol/L HCl, saturated NaHCO3 and saturated NaCl aqueous solution twice respectively. After that, the ethyl acetate layers are combined, dried over anhydrous Na2SO4 and the solvent is removed under reduced pressure, and the residue is purified by reduced pressure column chromatography (petroleum ether:ethyl acetate=2:1, V/V) to obtain a white solid (intermediate b) with a yield of 78.9%.

(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (Intermediate c)

0.38 g (1.78 mmol) of 4-(N-methyl) amino-N-Boc piperidine, 0.5 g (3.57 mmol) of K2CO3 and 40 mL of acetonitrile are added to a 100 mL single-necked round bottom flask. After stirring at normal temperature for 0.5-1 h, 1 g (1.96 mmol) of 3-(3-bromopropoxy)-5,7-dimethoxy-2-(3,4,5-trimethoxyphenyl)-4H-chromene-4-one (intermediate B) is added, followed by heating to 80° C., and stirring at this temperature for 4-6 h. the reaction is monitored by TLC, when the reaction is finished, cooled to room temperature, filtered to remove potassium carbonate and solid impurities, and the solvent is removed under reduced pressure to obtain a crude product (intermediate c) in the form of a burgundy oil for later use, yield: 91.7%.

(5) Preparation of hydrochloride (Intermediate d) of 5,7-dimethoxy-3-(3-(methyl (piperidin-4-yl) amino) propoxy)-2-(3,4,5-trimethoxyphenyl)-4H-chromene-4-one In Step 3, tert-butyl 4-((3-(5,7-dimethoxy-4-oxo-2-(3,4,5-trimethoxyphenyl)-4H-benzopyran-3-yl) oxy) propyl) (methyl) amino tert-butyl) piperidine-1-carboxylic acid (intermediate c) is dissolved in a 100 mL single-necked round bottom flask with about 30 mL methanol, then 10 ml of 6 mol/L methanol hydrochloride solution is added and stirred at room temperature for about 2 hours. The reaction is monitored by TLC, when the reaction is finished, a small amount of methanol is added to dissolve after the solvent is removed under reduced pressure, then 20 mL of ethyl acetate is added, and the mixture is continuously stirred until a yellow solid is precipitated, filtered, washed with ethyl acetate and dichloromethane respectively, and naturally dried to obtain a yellow solid (intermediate d), yield: 93.2%.

(6) Preparation of 5,7-dimethoxy-3-(3-(N-methyl (1-(4-methylbenzenesulfonyl) piperidyl)) amino) propoxy)-2-(3,4,5-trimethoxyphenyl)-4H-chromene-4-one (Target Compound I1)

0.5 g (0.86 mmol) of 5,7-dimethoxy-3-(3-(methyl (piperidin-4-yl) amino) propoxy)-2-(3,4,5-trimethoxyphenyl)-4H-chromene-4-one hydrochloride (intermediate d), 0.36 g (2.59 mmol) of K2CO3 and 20 ml of anhydrous ethanol are added into a 50 mL single-necked round bottom flask, and stirring at room temperature is carried out until there is a large amount of white solid, then 0.16 g (0.86 mmol) of p-toluenesulfonyl chloride is added, and stirring is continued for about 2 hours. The reaction is monitored by TLC and when it finished, the mixture is poured into 100 mL of water, extracted with dichloromethane (3×20 mL), the organic layers are combined, washed with saturated brine (3×20 mL), dried over anhydrous sodium sulfate, filtrated and the solvent is removed under reduced pressure to obtain a crude product, which is purified by column chromatography (ethyl acetate:methanol=5:1~1:10, V/V) to obtain the target compound I1, yield: 48.2%.

Embodiment 2

The preparation method of 5,7-dimethoxy-3-(3-(N-methyl (1-(naphthalene-2-ylsulfonyl) piperidyl)) amino) propoxy)-2-(3,4,5-trimethoxyphenyl)-4H-chromene-4-one (target compound I2) is as follows:
(1) Preparation of 3-hydroxy-3',4',5',5,7-pentamethoxy myricetin (intermediate a):
    As in step (1) of Embodiment 1.
(2) Preparation of 3-(3-bromopropoxy)-5,7-dimethoxy-2-(3, 4,5-trimethoxyphenyl)-4H-chromene-4-one (intermediate b):
    As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
    As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
    As in step (4) of Embodiment 1.
(5) Preparation of 5,7-dimethoxy-3-(3-(N-methyl (1-(naphthalene-2-ylsulfonyl) piperidinyl)) amino) propoxy)-2-(3, 4,5-trimethoxyphenyl)-4H-chromene-4-one (target compound I2):
    As in step (5) of Embodiment 1, the difference is that naphthalene-2-sulfonyl chloride is used as the raw material, yield: 66.9%.

Embodiment 3

The preparation method of 5,7-dimethoxy-3-(3-(N-methyl (1-(4-fluorophenyl sulfonyl) piperidyl)) amino) propoxy)-2-(3,4,5-trimethoxyphenyl)-4H-chromene-4-one (target compound I3) is as follows:
(1) Preparation of 3-hydroxy-3',4',5',5,7-pentamethoxy myricetin (intermediate a):
    As in step (1) of Embodiment 1.
(2) Preparation of 3-(3-bromopropoxy)-5,7-dimethoxy-2-(3, 4,5-trimethoxyphenyl)-4H-chromene-4-one (intermediate b):
    As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
    As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
    As in step (4) of Embodiment 1.
(5) Preparation of 5,7-dimethoxy-3-(3-(N-methyl (1-(4-fluorophenyl sulfonyl) piperidyl)) amino) propoxy)-2-(3, 4,5-trimethoxyphenyl)-4H-chromene-4-one (target compound I3):
    As in step (5) of Embodiment 1, the difference is that 4-fluorobenzenesulfonyl chloride is used as the raw material, yield: 45.3%.

Embodiment 4

The preparation method of 5,7-dimethoxy-3-(3-(N-methyl (1-(thiophene-2-ylsulfonyl) piperidyl)) amino) propoxy)-2-(3,4,5-trimethoxyphenyl)-4H-chromene-4-one (target compound I4) is as follows:
(1) Preparation of 3-hydroxy-3',4',5',5,7-pentamethoxy myricetin (intermediate a):
    As in step (1) of Embodiment 1.
(2) Preparation of 3-(3-bromopropoxy)-5,7-dimethoxy-2-(3, 4,5-trimethoxyphenyl)-4H-chromene-4-one (intermediate B):
    As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
    As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
    As in step (4) of Embodiment 1.
(5) Preparation of 5,7-dimethoxy-3-(3-(N-methyl (1-(thiophene-2-ylsulfonyl) piperidyl)) amino) propoxy)-2-(3,4, 5-trimethoxyphenyl)-4H-chromene-4-one (target compound I4):
    As in step (5) of Embodiment 1, the difference is that thiophenesulfonyl chloride is used as the raw material, yield: 63.3%.

Embodiment 5

The preparation method of 5,7-dimethoxy-3-(3-(N-methyl(1-(4-methoxybenzenesulfonyl) piperidyl)) amino) propoxy)-2-(3,4,5-trimethoxyphenyl)-4H-chromene-4-one (target compound I5) is as follows:

(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl(1-(4-methoxybenzenesulfonyl) piperidinyl)) amino) propoxy)-2-(3,4,5-trimethoxyphenyl)-4H-chromene-4-one (target compound I5):
As in step (5) of Embodiment 1, the difference is that 4-methoxybenzenesulfonyl chloride is used as the raw material, yield: 62.4%.

Embodiment 6

The preparation method of 5,7-dimethoxy-3-(3-(N-methyl (1-(4-nitrobenzenesulfonyl) piperidyl)) amino) propoxy)-2-(3,4,5-trimethoxyphenyl)-4H-chromene-4-one (target compound I6) is as follows:
(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl (1-(4-nitrobenzenesulfonyl) piperidinyl)) amino) propoxy)-2-(3,4,5-trimethoxyphenyl)-4H-chromene-4-one (target compound I6):
As in step (5) of Embodiment 1, the difference is that 4-nitrobenzenesulfonyl chloride is used as the raw material, yield: 95.8%.

Embodiment 7

The preparation method of 5,7-dimethoxy-3-(3-(N-methyl (1-(benzenesulfonyl) piperidinyl)) amino) propoxy)-2-(3,4,5-trimethoxyphenyl)-4H-chromene-4-one (target compound I7) is as follows:
(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl (1-(benzenesulfonyl) piperidinyl)) amino) propoxy)-2-(3,4,5-trimethoxyphenyl)-4H-chromene-4-one (target compound I7):
As in step (5) of Embodiment 1, the difference is that benzenesulfonyl chloride is used as the raw material, yield: 55.3%.

Embodiment 8

The preparation method of 5,7-dimethoxy-3-(3-(N-methyl (1-(pyridine-2-ylsulfonyl) piperidyl)) amino) propoxy)-2-(3,4,5-trimethoxyphenyl)-4H-chromene-4-one (target compound I8) is as follows:
(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl (1-(pyridine-2-ylsulfonyl) piperidyl)) amino) propoxy)-2-(3,4,5-trimethoxyphenyl)-4H-chromene-4-one (target compound I8):
As in step (5) of Embodiment 1, the difference is that pyridine-2-sulfonyl chloride is used as the raw material, yield: 47.6%.

Embodiment 9

The preparation method of 5,7-dimethoxy-3-(3-(N-methyl (1-(quinoline-7-ylsulfonyl) piperidyl)) amino) propoxy)-2-(3,4,5-trimethoxyphenyl)-4H-chromene-4-one (target compound I9) is as follows:
(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl)

(methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl (1-(quinoline-7-ylsulfonyl) piperidinyl)) amino) propoxy)-2-(3,4,5-trimethoxyphenyl)-4H-chromene-4-one (target compound I9):
As in step (5) of Embodiment 1, the difference is that quinoline-7-sulfonyl chloride is used as the raw material, yield: 44.7%.

Embodiment 10

The preparation method of 5,7-dimethoxy-3-(3-(N-methyl (1-(2-nitrobenzenesulfonyl) piperidyl)) amino) propoxy)-2-(3,4,5-trimethoxyphenyl)-4H-chromene-4-one (target compound I10) is as follows:
(1) Preparation of 3-hydroxy-3',4',5',5,7-pentamethoxy myricetin (intermediate a):
As in step (1) of Embodiment 1.
(2) Preparation of 3-(3-bromopropoxy)-5,7-dimethoxy-2-(3,4,5-trimethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 5,7-dimethoxy-3-(3-(N-methyl (1-(2-nitrobenzenesulfonyl) piperidinyl)) amino) propoxy)-2-(3,4,5-trimethoxyphenyl)-4H-chromene-4-one (target compound I10):
As in step (5) of Embodiment 1, the difference is that 2-nitrobenzenesulfonyl chloride is used as the raw material, yield: 45.5%.

Embodiment 11

The preparation method of 5,7-dimethoxy-3-(4-(N-methyl (1-(4-methylbenzenesulfonyl) piperidyl)) amino) butoxy)-2-(3,4,5-trimethoxyphenyl)-4H-chromene-4-one (target compound I11) is as follows:
(1) Preparation of 3-hydroxy-3',4',5',5,7-pentamethoxy myricetin (intermediate a):
As in step (1) of Embodiment 1.
(2) Preparation of 3-(4-bromobutoxy)-5,7-dimethoxy-2-(3,4,5-trimethoxyphenyl)-4H-chromene-4-one (intermediate b):
As in step (2) of Embodiment 1. The difference is that 1,4-dibromobutane is used as a raw material.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
As in step (4) of Embodiment 1.
(5) Preparation of 5,7-dimethoxy-3-(4-(N-methyl (1-(4-methylbenzenesulfonyl) piperidinyl)) amino) butoxy)-2-(3,4,5-trimethoxyphenyl)-4H-chromene-4-one (target compound I11):
As in step (5) of Embodiment 1, yield: 33.1%.

Embodiment 12

The preparation method of 5,7-dimethoxy-3-(4-(N-methyl (1-(naphthalene-2-ylsulfonyl) piperidyl)) amino) butoxy)-2-(3,4,5-trimethoxyphenyl)-4H-chromene-4-one (target compound I12) is as follows:
(1) Preparation of 3-hydroxy-3',4',5',5,7-pentamethoxy myricetin (intermediate a):
As in step (1) of Embodiment 1.
(2) Preparation of 3-(4-bromobutoxy)-5,7-dimethoxy-2-(3,4,5-trimethoxyphenyl)-4H-chromene-4-one (intermediate b):
As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
As in step (4) of Embodiment 1.
(5) Preparation of 5,7-dimethoxy-3-(4-(N-methyl (1-(naphthalene-2-ylsulfonyl) piperidinyl)) amino) butoxy)-2-(3,4,5-trimethoxyphenyl)-4H-chromene-4-one (target compound I12):
As in step (5) of Embodiment 2, yield: 33.6%.

Embodiment 13

The preparation method of 5,7-dimethoxy-3-(4-(N-methyl (1-(3-fluorophenyl sulfonyl) piperidyl)) amino) butoxy)-2-(3,4,5-trimethoxyphenyl)-4H-chromene-4-one (target compound I13) is as follows:
(1) Preparation of 3-hydroxy-3',4',5',5,7-pentamethoxy myricetin (intermediate a):
As in step (1) of Embodiment 1.
(2) Preparation of 3-(4-bromobutoxy)-5,7-dimethoxy-2-(3,4,5-trimethoxyphenyl)-4H-chromene-4-one (intermediate b):
As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidin-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
As in step (4) of Embodiment 1
(5) Preparation of 5,7-dimethoxy-3-(4-(N-methyl (1-(4-fluorophenyl sulfonyl) piperidyl)) amino) butoxy)-2-(3,4,5-trimethoxyphenyl)-4H-chromene-4-one (target compound I13):
As in step (5) of Embodiment 3, yield: 36.0%.

Embodiment 14

The preparation method of 5,7-dimethoxy-3-(4-(N-methyl (1-(thiophene-2-ylsulfonyl) piperidyl)) amino)

butoxy)-2-(3,4,5-trimethoxyphenyl)-4H-chromene-4-one (target compound I14) is as follows:
(1) Preparation of 3-hydroxy-3',4',5',5,7-pentamethoxy myricetin (intermediate a):
   As in step (1) of Embodiment 1.
(2) Preparation of 3-(4-bromobutoxy)-5,7-dimethoxy-2-(3,4,5-trimethoxyphenyl)-4H-chromene-4-one (intermediate b):
   As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
   As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
   As in step (4) of Embodiment 1.
(5) Preparation of 5,7-dimethoxy-3-(4-(N-methyl (1-(thiophene-2-ylsulfonyl) piperidinyl)) amino) butoxy)-2-(3,4,5-trimethoxyphenyl)-4H-chromene-4-one (target compound I14):
   As in step (5) of Embodiment 4, yield: 58.6%.

Embodiment 15

The preparation method of 5,7-dimethoxy-3-(4-(N-methyl(1-(4-methoxybenzenesulfonyl) piperidyl)) amino) butoxy)-2-(3,4,5-trimethoxyphenyl)-4H-chromene-4-one (target compound I15) is as follows:
(1) Preparation of 3-hydroxy-3',4',5',5,7-pentamethoxy myricetin (intermediate a):
   As in step (1) of Embodiment 1.
(2) Preparation of 3-(4-bromobutoxy)-5,7-dimethoxy-2-(3,4,5-trimethoxyphenyl)-4H-chromene-4-one (intermediate b):
   As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
   As in step (3) of Embodiment 1.
(4) Preparation of hydrochloride (intermediate d) of 5,7-dimethoxy-3-(4-(methyl (piperidin yl) amino) butoxy)-2-(3,4,5-trimethoxyphenyl)-4H-chromene-4-one:
   As in step (4) of Embodiment 1.
(5) Preparation of 5,7-dimethoxy-3-(4-(N-methyl(1-(4-methoxybenzenesulfonyl) piperidinyl)) amino) butoxy)-2-(3,4,5-trimethoxyphenyl)-4H-chromene-4-one (target compound I15):
   As in step (5) of Embodiment 5, yield: 61.2%.

Embodiment 16

The preparation method of 5,7-dimethoxy-3-(4-(N-methyl (1-(4-nitrobenzenesulfonyl) piperidyl)) amino) butoxy)-2-(3,4,5-trimethoxyphenyl)-4H-chromene-4-one (target compound I16) is as follows:
(1) Preparation of 3-hydroxy-3',4',5',5,7-pentamethoxy myricetin (intermediate a):
   As in step (1) of Embodiment 1.
(2) Preparation of 3-(4-bromobutoxy)-5,7-dimethoxy-2-(3,4,5-trimethoxyphenyl)-4H-chromene-4-one (intermediate b):
   As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
   As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
   As in step (4) of Embodiment 1.
(5) Preparation of 5,7-dimethoxy-3-(4-(N-methyl (1-(4-nitrobenzenesulfonyl) piperidinyl)) amino) butoxy)-2-(3,4,5-trimethoxyphenyl)-4H-chromene-4-one (target compound I16):
   As in step (5) of Embodiment 6, yield: 49.5%.

Embodiment 17

The preparation method of 5,7-dimethoxy-3-(4-(N-methyl (1-(benzenesulfonyl) piperidinyl)) amino) butoxy)-2-(3,4,5-trimethoxyphenyl)-4H-chromene-4-one (target compound I17) is as follows:
(1) Preparation of 3-hydroxy-3',4',5',5,7-pentamethoxy myricetin (intermediate a):
   As in step (1) of Embodiment 1.
(2) Preparation of 3-(4-bromobutoxy)-5,7-dimethoxy-2-(3,4,5-trimethoxyphenyl)-4H-chromene-4-one (intermediate b):
   As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
   As in step (3) of Embodiment 1.
(4) Preparation of hydrochloride (intermediate d) of 5,7-dimethoxy-3-(4-(methyl (piperidin yl) amino) butoxy)-2-(3,4,5-trimethoxyphenyl)-4H-chromene-4-one:
   As in step (4) of Embodiment 1.
(5) Preparation of 5,7-dimethoxy-3-(4-(N-methyl (1-(benzenesulfonyl) piperidinyl)) amino) butoxy)-2-(3,4,5-trimethoxyphenyl)-4H-chromene-4-one (target compound I17):
   As in step (5) of Embodiment 7, yield: 49.5%.

Embodiment 18

The preparation method of 5,7-dimethoxy-3-(4-(N-methyl (1-(pyridine-2-ylsulfonyl) piperidyl)) amino) butoxy)-2-(3,4,5-trimethoxyphenyl)-4H-chromene-4-one (target compound I18) is as follows:
(1) Preparation of 3-hydroxy-3',4',5',5,7-pentamethoxy myricetin (intermediate a):
   As in step (1) of Embodiment 1.
(2) Preparation of 3-(4-bromobutoxy)-5,7-dimethoxy-2-(3,4,5-trimethoxyphenyl)-4H-chromene-4-one (intermediate b):
   As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
   As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
   As in step (4) of Embodiment 1.
(5) Preparation of 5,7-dimethoxy-3-(4-(N-methyl (1-(pyridine-2-ylsulfonyl) piperidyl)) amino) butoxy)-2-(3,4,5- trimethoxyphenyl)-4H-chromene-4-one (target compound I18):
As in step (5) of Embodiment 8, yield: 72.2%.

Embodiment 19

The preparation method of 5,7-dimethoxy-3-(4-(N-methyl (1-(quinoline-7-ylsulfonyl) piperidyl)) amino) butoxy)-2-(3,4,5-trimethoxyphenyl)-4H-chromene-4-one (target compound I19) is as follows:
(1) Preparation of 3-hydroxy-3',4',5',5,7-pentamethoxy myricetin (intermediate a):
As in step (1) of Embodiment 1.
(2) Preparation of 3-(4-bromobutoxy)-5,7-dimethoxy-2-(3,4,5-trimethoxyphenyl)-4H-chromene-4-one (intermediate b):
As in step (2) of Embodiment 11.
(3) Preparation of 4-(4-((5,7-dimethoxy-4-oxo-2-(3,4,5-trimethoxyphenyl)-4H-benzopyran-3-yl-oxy)butyl (methyl)amino tert-butyl) (intermediate c) piperidine-1-carboxylic acid:
As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
As in step (4) of Embodiment 1.
(15) Preparation of 5,7-dimethoxy-3-(4-(N-methyl(1-(quinoline-7-ylsulfonyl) piperidinyl)) amino) butoxy)-2-(3,4,5-trimethoxyphenyl)-4H-chromene-4-one (target compound I19):
As in step (5) of Embodiment 9, yield: 98.2%.

Embodiment 20

T The preparation method of 5,7-dimethoxy-3-(4-(N-methyl (1-(2-nitrobenzenesulfonyl) piperidyl)) amino) butoxy)-2-(3,4,5-trimethoxyphenyl)-4H-chromene-4-one (target compound I20) is as follows:
(1) Preparation of 3-hydroxy-3',4',5',5,7-pentamethoxy myricetin (intermediate a):
As in step (1) of Embodiment 1.
(2) Preparation of 3-(4-bromobutoxy)-5,7-dimethoxy-2-(3,4,5-trimethoxyphenyl)-4H-chromene-4-one (intermediate b):
As in step (2) of Embodiment 11.
(3) Preparation of 4-(4-((5,7-dimethoxy-4-oxo-2-(3,4,5-trimethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:
As in step (4) of Embodiment 1.
(5) Preparation of 5,7-dimethoxy-3-(4-(N-methyl(1-(2-nitrobenzenesulfonyl) piperidinyl)) amino) butoxy)-2-(3,4,5-trimethoxyphenyl)-4H-chromene-4-one (target compound I20):
As in step (5) of Embodiment 10, yield: 60.8%.

The physicochemical properties and mass spectrum data of the synthesized sulfonamide-containing 4-(N-methyl) aminopiperidine myricetin derivative are shown in Table 1, and the nuclear magnetic resonance hydrogen spectrum (1H NMR) and carbon spectrum (13C NMR) data are shown in Table 2.

TABLE 1

Physical and Chemical Properties of Compounds I1-I20 of Embodiments

| Compound | n | R-gene | Mass Spectromerty, m/z (calcd) | Character | Melting Pont/° C. | Yied/% |
|---|---|---|---|---|---|---|
| I1 | 3 | 4-Methylphenyl | 697.27734 (697.27894) [M ± N]± | Grey Solid | 81.2-81.9 | 48.2 |
| I2 | 3 | Napathalene-2-yl | 733.27704 (733.27894) [M ± N]± | Grey Solid | 87.5-88.2 | 66.9 |
| I3 | 3 | 4-Florophenyl | 701.25195 (701.25387) [M ± N]± | White Sold | 101.5-102.1 | 45.3 |
| I4 | 3 | Thiophene-2-yl | 689.21826 (689.21971) [M ± N]± | Grey Solid | 107.8-108.5 | 63.3 |
| I5 | 3 | 4-Methoxyphenyl | 713.27179 (713.27386) [M ± N]± | White Solid | 89.1-89.7 | 62.4 |
| I6 | 3 | 4-Nitrophenyl | 728.24634 (728.24837) [M ± N]± | White Solid | 99.3-100.2 | 95.8 |
| I7 | 3 | Phenyl | 683.26147 (683.26329) [M ± N]± | White Solid | 78.6-79.2 | 55 3 |
| I8 | 3 | Pyridine-2-yl | 684.25671 (684.25854) [M ± N]± | White Solid | 112.3-112.7 | 47.6 |
| I9 | 3 | Quinoline-7-yl | 734.27216 (734.27419) [M ± N]± | White Solid | 133.6-134.2 | 44.7 |
| I10 | 3 | 2-Nitrophenyl | 728.24579 (728.24837) [M ± N]± | White Solid | 162.9-163.3 | 45.5 |
| I11 | 4 | 4-Methylphenyl | 711.29266 (711.29459) [M ± N]± | Yellow Solid | 77.0-77.9 | 331 |
| I12 | 4 | Naphthalene-2-yl | 747.29272 (747.29459) [M ± N]± | Yellow Solid | 85.6-86.1 | 33.6 |
| I13 | 4 | 4-Florophenyl | 715.26776 (715.26952) [M ± N]± | Yellow Solid | 88.1-88.6 | 36.0 |
| I14 | 4 | Thiophene-2-yl | 703.23364 (703.23536) [M ± N]± | Yellow Solid | 92.1-92.9 | 58.6 |
| I15 | 4 | 4-Methoxyphenyl | 727.28790 (727.28951) [M ± N]± | Yellow Solid | 93.4-94.7 | 61.2 |
| I16 | 4 | 4-Nitrophenyl | 742.26184 (742.26402) [M ± N]± | Yellow Solid | 148.9-149.6 | 49.5 |

TABLE 1-continued

Physical and Chemical Properties of Compounds I1-I20 of Embodiments

| Compound | n | R-gene | Mass Spectromerty, m/z (calcd) | Character | Melting Pont/° C. | Yied/% |
|---|---|---|---|---|---|---|
| I17 | 4 | Phenyl | 697.27740 (697.27894 [M ± N]$^±$) | Yellow Solid | 98.3-99.7 | 57.2 |
| I18 | 4 | Pyridine-2-yl | 698.27246 (698.27419 [M ± N]$^±$) | Yellow Solid | 72.7-73.1 | 72.2 |
| I19 | 4 | Quinoline-7-yl | 748.28809 (748.28984 [M ± N]$^±$) | Yellow Solid | 123.6-124.2 | 98.2 |
| I20 | 4 | 2-Nitrophenyl | 742.26215 (743.26402 [M ± N]$^±$) | Yellow Solid | 71.7-72.2 | 60.8 |

TABLE 2

Nuclear Magnetic Resonance Spectrum Data of Compounds I1-I20 of embodiments

| Compound | $^1$H NMR, $^{13}$C NMR (TMS is internal standard) |
|---|---|
| I1 | $^1$H NMR (400 MHz, DMSO) δ 7.60 (d, J = 8.2 Hz, 2H, Ph-H), 7.43 (d, J = 8.0 Hz, 2H, Ph-H), 7.34 (s, 2H, ph-H), 6.82 (s, 1H, Ph-H), 6.49 (d, J = 1.9 Hz, 1H, Ph-H), 3.94 (t, J = 6.1 Hz, 2H, —O—CH$_2$CH$_2$CH$_2$CH$_2$—N—), 3.90 (s, 3H, Ph-OCH$_3$), 3.84 (s, 9H, Ph-OCH$_3$), 3.73 (s, 3H, Ph-OCH$_3$), 3.58 (d, J = 11.6 Hz, 2H, Piperidinyl-H), 2.40 (s, 3H, Ph-CH$_3$), 2.33 (s, 2H, —O—CH$_2$CH$_2$CH$_2$—N—), 2.16 (t, J = 11.0 Hz, 3H, Piperidinyl-H), 2.01 (s, 3H, N—CH$_3$), 1.66 (dd, J = 12.6, 6.2 Hz, 2H, —O—CH$_2$CH$_2$CH$_2$—N—), 1.56 (d, J = 11.3 Hz, 2H, Piperidinyl-H), 1.35 (dt, J = 11.5, 6.1 Hz, 2H, Piperidinyl-H) $^{13}$C NMR (101 MHz, DMSO) δ 172.66, 164.19, 160.75, 158.62, 153.12, 151.97, 143.87, 140.43, 139.86, 133.15, 130.24, 127.91, 126.10, 108.94, 106.35, 96.37, 93.55, 70.71, 60.64, 59.48, 56.50, 50.43, 46.01, 37.30, 28.41, 27.07, 21.44 |
| I2 | $^1$H NMR (400 MHz, DMSO) δ 8.43 (s, 1H, Naphthyl-H), 8.21 (d, J = 7.7 Hz, 1H, Naphthyl-H), 8.16 (d, J = 8.7 Hz, 1H, Naphthyl-H), 8.07 (d, J = 8.1 Hz, 1H, Naphthyl-H), 7.77-7.72 (m, 2H, Naphthyl-H), 7.69 (dd, J 12.5, 4.1 Hz, 1H Naptyl-H), 7.32 (s, 2H, Ph-H), 6.81 (d, J = 1.4 Hz, 1H, Ph-H), 6.48 (d, J = 2.0 Hz, 1H, Ph-H), 3.94-3.88 (m, 5H, —O—CH$_2$CH$_2$CH$_2$—N—, Ph-OCH$_3$), 3.82 (d, J = 5.7 Hz, 9H, Ph-OCH$_3$), 3.72 (s, 2H, Piperidinyl-H), 3.68 (s, 3H, Ph-OCH$_3$), 2.29 (dd, J = 36.5, 25.0 Hz, 4H, —O—CH$_2$CH$_2$CH$_2$—N—, Piperidinyl-H), 2.13 (d, J = 2.9 Hz, 1H, Piperidinyl-H), 1.99 (s, 3H, N—CH$_3$), 1.74-1.51 (m, 4H, —O—CH$_2$CH$_2$CH$_2$—N—, Piperidinyl-H), 1.37 (dd, J = 21.5, 11.0 Hz, 2H, Piperidinyl-H). $^{13}$C NMR (101 MHz, DMSO) δ 172.66, 164.20, 160.76, 158.62, 153.11, 152.00, 140.40, 138.89, 134.88, 133.43, 132.33, 129.78, 129.75, 129.42, 129.00, 128.09, 126.07, 123.33, 108.94, 106.39, 96.38, 93.57, 70.67, 68.22, 60.60, 59.49, 56.54, 56.50, 50.48, 46.09, 37.19, 27.09 |
| I3 | $^1$H NMR (400 MHz, DMSO) δ 7.80 (dd, J = 8.7, 5.2 Hz, 2H, Ph-H), 7.49 (t, J = 8.8 Hz, 2H, Ph-H), 7.33 (s, 2H, Ph-H), 6.82 (s, 1H, Ph-H), 6.49 (d, J = 1.7 Hz, 1H, Ph-H), 3.94 (t, J = 6.0 Hz, 2H, —O—CH$_2$CH$_2$CH$_2$—N—), 3.90 (s, 3H, Ph-OCH$_3$), 3.84 (d, J = 2.5 Hz, 9H, Ph-OCH$_3$), 3.73 (s, Ph-OCH$_3$), 3.60 (d, J = 11.5 Hz, 2H, Piperidinyl-H), 2.33 (t, J = 6.7 Hz, 2H, —O—CH$_2$CH$_2$CH$_2$—N—, 2.22-2.10 (m, 3H, Piperidinyl-H), 2.01 (s, 3H, N—CH$_3$), 1.67 (dd, J = 12.5, 6.0 Hz, 2H, —O—CH$_2$CH$_2$CH$_2$—N—), 1.57 (d, J = 11.2 Hz, 2H, Piperidinyl-H), 1.35 (qd, J = 12.2, 3.2 Hz, 2H, Piperidinyl-H), $^{13}$C NMR (101 MHz, DMSO) δ 172.67, 166.28, 163.78, 160.72, 158.62, 153.10, 152.00, 140.41, 139.77, 132.42, 130.99, 130.90, 128.36, 128.28, 126.11, 117.13, 116.91, 114.94, 114.73, 108.91, 106.29, 96.36, 93.53, 70.68, 60.64, 59.43, 56.51, 50.50, 46.03, 37.17, 28.40, 27.01 $^{19}$F NMR (472 MHz, Chloroform) δ −108.20 |
| I4 | $^1$H NMR (400 MHz, DMSO) δ 8.04 (dd, J = 5.0, 1.2 Hz, 1H, Thienyl-H), 7.62 (dd, J = 3.7, 1.1 Hz, 1H, Thienyl-H), 7.34 (s, 2H, Ph-H), 7.28 (dd, J = 4.9, 3.8 Hz, 1H, Thienyl-H), 6.84 (d, J = 2.1 Hz, 1H, Ph-H), 6.49 (d, J = 2.2 Hz, 1H, Ph-H), 3.94 (t, J = 6.0 Hz, 2H, —O—CH$_2$CH$_2$CH$_2$—N—), 3.90 (s, 3H, Ph-OCH$_3$), 3.85 (s, 6H, Ph-OCH$_3$), 3.84 (s, 3H, Ph-OCH$_3$), 3.73 (s, 3H, Ph-OCH$_3$), 3.61 (d, J = 11.2 Hz, 2H, |

TABLE 2-continued

Nuclear Magnetic Resonance Spectrum Data of Compounds I1-I20 of embodiments

| Compound | $^1$H NMR, $^{13}$C NMR (TMS is internal standard) |
|---|---|
| | Piperidinyl-H), 2.44 (s, 1H, Piperidinyl-H), 2.29 (t, J = 11.1 Hz, 3H, —O—CH$_2$CH$_2$CH$_2$—N—, Piperidinyl-H), 2.10 (s, 3H, N—CH$_3$), 1.67 (dd, J = 19.1, 12.3 Hz, 4H, —O—CH$_2$CH$_2$CH$_2$—N—, Piperidinyl-H), 1.51-1.33 (m, 2H, Piperidinyl-H), 1.06 (t, J = 7.0 Hz, 1H, Piperidinyl-H).<br>$^{13}$C NMR (101 MHz, DMSO) δ 172.72, 164.24, 160.72, 158.64, 153.13, 152.09, 140.35, 139.80, 135.79, 134.14, 133.33, 128.76, 108.87, 106.26, 96.40, 93.55, 70.56, 60.676, 59.49, 56.56, 56.53, 50.56, 45.98, 37.14, 26.74, 19.04. |
| I5 | $^1$H NMR (400 MHz, DMSO) δ 7.68-7.61 (m, 2H, Ph-H), 7.34 (s, 2H, Ph-H), 7.18-7.12 (m, 2H, Ph-H), 6.83 (d, J = 2.2 Hz, 1H, Ph-H), 6.49 (d, J = 2.2 Hz, 1H, Ph-H), 3.94 (t, J = 6.1 Hz, 2H, —O—CH$_2$CH$_2$CH$_2$—N—), 3.90 (s, 3H, Ph-OCH$_3$), 3.84 (t, J = 1.9 Hz, 12H, Ph-OCH$_3$), 3.73 (s, 3H, Ph-OCH$_3$), 3.56 (d, J = 11.6 Hz, 2H, Piperidinyl-H), 2.33 (t, J = 7.0 Hz, 2H, —O—CH$_2$CH$_2$CH$_2$—N—), 2.19-2.07 (m, 3H, Piperidinyl-H), 2.01 (s, 3H, N—CH$_3$), 1.71-1.62 (m, 2H, —O—CH$_2$CH$_2$CH$_2$—N—), 1.56 (d, J = 10.9 Hz, 2H, Piperidinyl-H), 1.35 (qd, J = 12.2, 3.6 Hz, 2H, Piperidinyl-H).<br>$^{13}$C NMR (101 MHz, DMSO) δ 172.66, 164.18, 163.09, 160.73, 158.62, 153.10, 151.97, 140.43, 139.79, 130.09, 127.48, 126.10, 114.92, 108.91, 106.29, 96.36, 93.53, 70.71, 60.64, 59.50, 56.51, 56.15, 50.43, 46.05, 37.29, 28.41, 27.04. |
| I6 | $^1$H NMR (400 MHz, DMSO) δ 8.48-8.42 (m, 2H, Ph-H), 8.03-7.96 (m, 2H, Ph-H), 7.33 (s, 2H, Ph-H), 6.82 (d, J = 2.2 Hz, 1H, Ph-H), 6.48 (d, J = 2.2 Hz, 1H, Ph-H), 3.94 (t, J = 6.1 Hz, 2H, —O—CH$_2$CH$_2$CH$_2$—N—), 3.90 (s, 3H, Ph-OCH$_3$), 3.84 (d, J = 2.1 Hz, 9H, Ph-OCH$_3$), 3.72 (s, 3H, Ph-OCH$_3$), 3.65 (d, J = 11.4 Hz, 2H, Piperidinyl-H), 2.37-2.24 (m, 4H, —O—CH$_2$CH$_2$CH$_2$—N—, Piperidinyl-H), 2.13 (dd, J = 15.2, 7.3 Hz, 1H, Piperidinyl-H), 2.01 (s, 3H, N—CH$_3$), 1.71-1.62 (m, 2H, —O—CH$_2$CH$_2$CH$_2$—N—), 1.58 (d, J = 11.0 Hz, 2H, Piperidinyl-H), 1.37 (qd, J = 12.3, 3.7 Hz, 2H, Piperidinyl-H).<br>$^{13}$C NMR (101 MHz, DMSO) δ 172.66, 164.18, 160.72, 158.61, 153.10, 151.97, 150.41, 141.74, 140.42, 139.76, 129.45, 126.11, 152.12, 108.90, 106.28, 96.35, 93.52, 70.68, 60.63, 59.31, 56.54, 56.51, 50.48, 46.00, 37.18, 28.41, 27.10. |
| I7 | $^1$H NMR (400 Mhz, DMSO) δ 7.71 (dd, J = 7.9, 6.7 Hz, 3H, Ph-H), 7.64 (dd, J = 10.6, 4.0 Hz, 2H, Ph-H), 7.33 (d, J = 1.8 Hz, 2H, Ph-H), 6.82 (d, J = 5.0 Hz, 1H, Ph-H), 6.48 (d, J = 4.6 Hz, 1H, Ph-H), 3.93 (t, J = 6.3 Hz, 2H, —O—CH$_2$CH$_2$CH$_2$—N—), 3.90 (d, J = 1.8 Hz, 3H, Ph-OCH$_3$), 3.84 (s, 9H, Ph-OCH$_3$), 3.72 (s, 3H, Ph-OCH$_3$), 3.60 (d, J = 11.5 Hz, 2H, Piperidinyl-H), 2.31 (t, J = 6.8 Hz, 2H, —O—CH$_2$CH$_2$CH$_2$—N—), 2.22-2.09 (m, 3H, Piperidinyl-H), 1.99 (s, 3H, N—CH$_3$), 1.71-1.62 (m, 2H, —O—CH$_2$CH$_2$CH$_2$—N—), 1.56 (d, J = 11.8 Hz, 2H, Piperidinyl-H), 1.40-1.29 (m, 2H, Piperidinyl-H).<br>$^{13}$C NMR (101 MHz, DMSO) δ 172.66, 160.70, 158.60, 153.09, 151.97, 140.41, 139.75, 136.01, 133.53, 129.83, 127.85, 126.10, 108.89, 106.24, 96.34, 93.51, 70.69, 60.64, 59.46, 56.49, 50.45, 46.03, 37.20, 28.40, 27.01. |
| I8 | $^1$H NMR (400 MHz, DMSO) δ 8.93-8.86 (m, 2H, Pyridiyl-H), 8.18-8.13 (m, 1H, Pyridiyl-H), 7.70 (ddd, J = 8.0, 4.8, 0.6 Hz, 1H, Pyridiyl-H), 7.33 (s, 2H, Ph-H), 6.83 (d, J = 2.2 Hz, 1H, Ph-H), 6.49 (d, J = 2.2 Hz, 1H, Ph-H), 3.94 (t, J = 6.1 Hz, 2H, —O—CH$_2$CH$_2$CH$_2$—N—), 3.90 (s, 3H, Ph-OCH$_3$), 3.71 (s, 3H, Ph-OCH$_3$), 3.65 (d, J = 11.7 Hz, 2H, Piperidinyl-H), 2.35-2.22 (m, 4H, —O—CH$_2$CH$_2$CH$_2$—N—, Piperidinyl-H), 2.19-2.10 (m, 1H, Piperidinyl-H), 2.00 (s, 3H, N—CH$_3$), 1.71-1.62 (m, 2H, —O—CH$_2$CH$_2$CH$_2$—N—), 1.60-1.53 (m, 2H, Piperidinyl-H), 1.35 (qd, J = 12.3, 3.8 Hz, 2H, Piperidinyl-H).<br>$^{13}$C NMR (101 MHz, DMSO) δ 172.66, 164.18, 160.71, 158.62, 154.10, 153.09, 152.01, 148.11, 140.40, 139.73, 135.99, 132.70, 126.10, 124.93, 108.89, 106.26, 96.35, 93.51, 70.67, 60.65, 59.34, 56.53, 56.49, 50.52, 45.94, 37.12, 28.41, 27.00. |
| I9 | $^1$H NMR (400 MHz, DMSO) δ 9.07 (dd, J = 4.2, 1.8 Hz, 1H, Quinolyl-H), 8.53 (dd, J = 8.4, 1.7 Hz, 1H, Quinolyl-H), 8.35 (dd, J = 7.4, 1.3 Hz, 1H, Quinolyl-H), 8.29 (dd, J = 8.2, 1.2 Hz, 1H, Quinolyl-H), 7.80-7.73 (m, 1H, Quinolyl-H), 7.69 (dd, J = 8.3, 4.2 Hz, 1H, Quinolyl-H), 7.33 (s, 2H, Ph-H), 6.82 (d, J = 2.1 Hz, 1H, Ph-H), 6.48 (d, J = 2.2 Hz, 1H, Ph-H), 3.94 (d, J = 6.0 Hz, 2H, —O—CH$_2$CH$_2$CH$_2$—N—), 3.90 (s, 3H, |

TABLE 2-continued

Nuclear Magnetic Resonance Spectrum Data of Compounds I1-I20 of embodiments

| Compound | ¹H NMR, ¹³C NMR (TMS is internal standard) |
|---|---|
|  | Ph-OCH₃), 3.89-3.85 (m, 2H, Piperidinyl-H), 3.83 (d, J = 2.1 Hz, 9H, Ph-OCH₃), 3.69 (s, 3H, Ph-OCH₃), 2.65 (t, J = 11.6 Hz, 2H, Piperidinyl-H), 2.32 (t, J = 6.4 Hz, 2H, —O—CH₂CH₂CH₂—N—), 2.19 (t, J = 9.3 Hz, 1H, Piperidinyl-H), 1.98 (s, 3H, N—CH₃), 1.67 (dd, J = 12.6, 6.1 Hz, 2H, —O—CH₂CH₂CH₂—N—), 1.54 (d, J = 11.1 Hz, 2H, Piperidinyl-H), 1.29 (t, J = 11.6, 5.9 Hz, 2H, Piperdinyl-H). ¹³C NMR (101 MHz, DMSO) δ 172.66, 164.17, 160.70, 158.60, 153.08, 151.97, 151.78, 143.80, 140.42, 139.73, 137.25, 136.71, 134.36, 132.93, 129.17, 126.21, 126.09, 122.88, 108.89, 106.23, 96.34, 93.51, 70.69, 60.58, 60.02, 56.49, 56.47, 50.56, 46.04, 37.05, 28.51, 27.83. |
| I10 | ¹H NMR (400 MHz, DMSO) δ 7.98 (t, J = 7.7 Hz, 2H, Ph-H), 7.88 (dtd, J = 18.1, 7.4, 1.2 Hz, 2H, Ph-H), 7.35 (s, 2H, Ph-H), 6.83 (d, J = 2.0 Hz, 1H, Ph-H), 6.49 (d, J = 2.0 Hz, 1H, Ph-H), 3.96 (t, J = 6.0 Hz, 2H, —O—CH₂CH₂CH₂—N—), 3.90 (s, 3H, Ph-OCH₃), 3.85 (s, 6H, Ph-OCH₃), 3.84 (s, 3H, Ph-OCH₃), 3.73 (s, 3H, Ph-OCH₃), 3.69 (d, J = 12.8 Hz, 2H, Piperidinyl-H), 2.65 (t, J = 11.4 Hz, 2H, Piperidinyl-H), 2.36 (t, J = 7.0 Hz, 2H, —O—CH₂CH₂CH₂—N—), 2.29 (t, J = 11.2 Hz, 1H, Piperidinyl-H), 2.02 (s, 3H, N—CH₃), 1.69 (dt, J = 12.8, 6.2 Hz, 2H, —O—CH₂CH₂CH₂—N—), 1.61 (d, J = 11.4 Hz, 2H, Piperidinyl-H), 1.34 (qd, J = 12.1, 2.9 Hz, 2H, Piperidinyl-H). ¹³C NMR (101 MHz, DMSO) δ 172.67, 164.20, 160.74, 158.63, 153.12, 152.01, 14.34, 140.46, 139.79, 135.19, 132.71, 130.75, 129.86, 126.12, 124.58, 108.92, 106.31, 96.38, 93.54, 70.72, 60.65, 59.39, 56.54, 56.51, 50.55, 45.83, 37.10, 28.49, 27.38. |
| I11 | ¹H NMR (400 MHz, DMSO) δ 7.60 (d, J = 7.1 Hz, 2H, Ph-H), 7.43 (d, J = 7.8 Hz, 2H, Ph-H), 7.37 (s, 2H, Ph-H), 6.84 (s, 1H, Ph-H), 6.49 (s, 1H, Ph-H), 3.93-3.81 (m, 14H, —O—CH₂CH₂CH₂CH₂—N—, Ph-OCH₃), 3.74 (s, 3H, Ph-OCH₃), 3.58 (d, J = 11.5 Hz, 2H, Piperidinyl-H), 2.39 (s, 3H, Ph-CH₃), 2.22 (dt, J = 23.5, 13.4 Hz, 5H, —O—CH₂CH₂CH₂CH₂—N—, Piperidinyl-H), 2.01 (s, 3H, N—CH₃), 1.64-1.52 (m, 4H, —O—CH₂CH₂CH₂CH₂—N—), 1.44-1.32 (m, 4H, Piperidinyl-H). ¹³C NMR (101 MHz, DMSO) δ 172.66, 164.18, 160.72, 158.61, 153.11, 152.00, 143.88, 140.42, 139.76, 133.04, 130.24, 127.93, 126.11, 108.90, 106.14, 96.37, 95.53, 72.00, 60.63, 59.39, 56.51, 56.48, 52.61, 46.06, 37.58, 27.75, 27.05, 23.87, 21.44. |
| I12 | ¹H NMR (400 MHz, DMSO) δ 8.42 (s, 1H, Naphthyl-H) 8.19 (d, J = 7.8 Hz, 1H, Naphthyl-H), 8.14 (d, J = 8.7 Hz, 1H, Naphthyl-H), 8.05 (d, J = 8.0 Hz, 1H, Naphthyl-H), 7.75-7.64 (m, 3H, Naphthyl-H), 7.34 (s, 2H, Ph-H), 6.80 (s, 1H, Ph-H), 6.45 (s, 1H, Ph-H), 3.92-3.85 (m, 5H, —O—CH₂CH₂CH₂CH₂—N—, Ph-OCH₃), 3.83 (s, 6H, Ph-OCH₃), 3.82 (s, 3H, Ph-OCH₃), 3.72 (s, 3H, Ph-OCH₃), 3.68 (s, 2H, Piperidinyl-H), 2.33-2.13 (m, 5H, —O—CH₂CH₂CH₂CH₂—N—, Piperidinyl-H), 2.00 (s, 3H, N—CH₃), 1.55 (dt, J = 13.9, 9.0 Hz, 4H, —O—CH₂CH₂CH₂CH₂—N—), 1.45-1.28 (m, 4H, Piperidinyl-H). ¹³C NMR (101 MHz, DMSO) δ 172.64, 164.15, 160.70, 158.58, 153.08, 151.92, 140.40, 139.77, 134.85, 133.31, 132.31, 129.76, 129.73, 129.40, 129.01, 128.08, 126.09, 123.33, 108.90, 106.13, 96.29, 93.49, 71.92, 60.59, 59.39, 56.45, 52.60, 46.12, 37.44, 27.71, 27.02, 23.70. |
| I13 | ¹H NMR (400 MHz, DMSO) δ 7.83-7.77 (m, 2H, Ph-H), 7.48 (t, J = 8.8 Hz, 2H, Ph-H), 7.36 (s, 2H, Ph-H), 6.84 (s, 1H, Ph-H), 6.49 (d, J = 2.0 Hz, 1H, Ph-H), 3.92-3.88 (m, 5H, —O—CH₂CH₂CH₂CH₂—N—, Ph-OCH₃), 3.85 (s, 6H, Ph-OCH₃), 3.84 (s, 3H, Ph-OCH₃), 3.74 (s, 3H, Ph-OCH₃), 3.61 (d, J = 11.6 Hz, 2H, Piperidinyl-H), 2.24 (dd, J = 15.1, 8.3 Hz, —O—CH₂CH₂CH₂CH₂—N—, Piperidinyl-H), 2.02 (s, 3H, N—CH₃), 165-1.53 (m, 4H, —O—CH₂CH₂CH₂CH₂—N—), 1.44-1.32 (m, 4H, Piperidinyl-H). ¹³C NMR (101 MHz, DMSO) δ 172.67, 166.27, 164.27, 164.19, 163.77, 160.72, 158.61, 153.11, 152.00, 140.42, 139.76, 132.45, 132.43, 131.00, 130.90, 128.35, 128.26, 126.12, 117.14, 116.91, 114.92, 114.71, 108.90, 106.16, 96.36, 93.54, 72.01, 60.63, 59.33, 56.59, 52.67, 46.07, 37.54, 27.76, 27.04, 23.88, 19.03. ¹⁹F NMR (376 MHz, DMSO) δ −106.09. |
| I14 | ¹H NMR (400 MHz, DMSO) δ 8.04 (dd, J = 5.0, 1.1 Hz, 1H, Thienyl-H), 7.62 (d, J = 3.6 Hz, 1H, Thienyl—H), 7.37 (s, 2H, Ph-H), 7.28 (dd, J = 4.8, 3.9 Hz, 1H, Thienyl-H), 6.84 (s, 1H, Ph-H), 6.49 (d, J = 2.0 Hz, 1H, Ph-H), 3.91 (d, J = 8.8 Hz, 5H, —O—CH₂CH₂CH₂CH₂—, Ph-OCH₃), 3.86 (s, 6H, Ph-OCH₃), 3.84 (s, 3H, Ph-OCH₃), 3.75 (s, 3H, Ph-OCH₃), 3.63 (d, J = 11.5 Hz, 2H, Piperidinyl-H), 2.49-2.26 (m, 5H, —O—CH₂CH₂CH₂CH₂—, Piperidinyl-H), 2.13 (s, 3H, N—CH₃), 1.73 (d, J = 10.5 Hz, 2H, —O—CH₂CH₂CH₂—N—), 1.65-1.56 (m, 2H, —O—CH₂CH₂CH₂CH₂—N ), 1.54-1.38 (m, 4H, Piperidinyl-H), ¹³C NMR (101 MHz, DMSO) δ 172.67, 164.20, 160.72, 158.62, 153.12, 152.03, |

TABLE 2-continued

Nuclear Magnetic Resonance Spectrum Data of Compounds
I1-I20 of embodiments

| Compound | ¹H NMR, ¹³C NMR (TMS is internal standard) |
|---|---|
| | 140.39, 139.77, 135.81, 134.15, 133.35, 128.76, 126.10, 108.89, 106.13, 96.38, 93.54, 71.87, 60.64, 59.44, 56.51, 52.65, 49.06, 46.00, 37.40, 27.67, 26.69, 23.40. |
| I15 | ¹H NMR (400 MHz, DMSO) δ 7.65 (d, J = 8.8 Hz, 2H, Ph-H), 7.37 (s, 2H, Ph-H), 7.14 (d, J = 8.8 Hz, 2H, Ph-H), 6.84 (d, J = 1.9 Hz, 1H, Ph-H), 6.49 (d, J = 2.1 Hz, 1H, Ph-H), 3.89 (d, J = 8.7 Hz, 5H, —O—CH₂CH₂CH₂CH₂—N—, Ph-OCH₃), 3.86 (s, 6H, Ph-OCH₃), 3.84 (s, 6H, Ph-OCH₃), 3.74 (s, 3H, Ph-OCH₃), 3.58 (d, J = 11.6 Hz, 2H, Piperidinyl-H), 2.21 (dt, J = 21.8, 8.6 Hz, 5H, —O—CH₂CH₂CH₂CH₂—N—, Piperidinyl-H), 2.02 (s, 3H, N—CH₃), 1.66-1.52 (m, 4H, —O—CH₂CH₂CH₂CH₂—N—), 1.46-1.30 (m, 4H, Piperidinyl-H). ¹³C NMR (101 MHz, DMSO) δ 172.66, 164.18, 163.08, 160.72, 158.61, 153.11, 151.99, 140.43, 139.76, 130.10, 127.47, 126.11, 114.91, 108.90, 106.14, 96.36, 93.53, 72.01, 60.63, 59.45, 56.48, 56.14, 52.65, 46.09, 37.58, 27.77, 27.04, 23.87. |
| I16 | ¹H NMR (400 MHz, DMSO) δ 8.44 (d, J = 8.8 Hz, 2H, Ph-H), 8.00 (d, J = 8.8 Hz, 2H, Ph-H), 7.36 (s, 2H, Ph-H), 6.83 (d, J = 2.2 Hz, 1H, Ph-H), 6.48 (d, J = 2.2 Hz, 1H, Ph-H), 3.89 (d, J = 9.0 Hz, 5H, —O—CH₂CH₂CH₂CH₂—N—, Ph-OCH₃), 3.86 (s, 6H, Ph-OCH₃), 3.84 (s, 3H, Ph-OCH₃), 3.74 (s, 3H, Ph-OCH₃), 3.66 (d, J = 11.4 Hz, 2H, Piperidinyl-H), 2.34 (dd, J = 11.5, 10.5 Hz, 2H, —O—CH₂CH₂CH₂CH₂—N—), 2.24 (dd, J = 14.7, 8.0 Hz, 3H, Piperidinyl-H), 2.02 (s, 3H, N—CH₃), 1.64 (d, J = 10.2 Hz, 2H, —O—CH₂CH₂CH₂CH₂—N—), 1.57 (dd, J = 14.3, 6.8 Hz, 2H, Piperidinyl-H), 1.46-132 (m, 4H, —O—CH₂CH₂CH₂CH₂—N—, Piperidinyl-H). 13C NMR (101 MHz, DMSO) δ 172.67, 164.19, 160.72, 158.60, 153.10, 151.98, 150.40, 141.79, 140.41, 139.77, 129.44, 126.11, 125.11, 108.90, 106.16, 96.35, 93.53, 72.00, 60.63, 59.16, 56.53, 56.49, 52.69, 46.03, 37.54, 27.77, 27.14, 23.87. |
| I17 | ¹H NMR (400 MHz, DMSO) δ 7.75-7.68 (m, 3H, Ph-H), 7.67-7.61 (m, 2H, Ph-H), 7.36 (s, 2H, Ph-H), 6.83 (d, J = 2.0 Hz, 1H, Ph-H), 6.49 (d, J = 2.2 Hz, 1H, Ph-H), 3.90 (d, J = 2.8 Hz, 5H, —O—CH₂CH₂CH₂CH₂—N—, Ph-OCH₃), 3.85 (s, 6H, Ph-OCH₃), 3.84 (s, 3H, Ph-OCH₃), 3.74 (s, 3H, Ph-OCH₃), 3.62 (d, J = 11.9 Hz, 2H, Piperidinyl-H), 2.27-2.18 (m, 5H, —O—CH₂CH₂CH₂CH₂—N—, Piperidinyl-H), 2.02 (s, 3H, N—CH₃), 1.65-1.52 (m, 4H, —O—CH₂CH₂CH₂CH₂—N—), 1.40 (dd, J = 1.79, 6.0 Hz, 4H, Piperidinyl-H). ¹³C NMR (101 MHz, DMSO) δ 172.66, 164.18, 160.71, 158.61, 153.10, 151.98, 140.42, 139.75, 136.06, 133.52, 129.83, 127.86, 126.11, 109.90, 106.13, 96.35, 93.52, 72.00, 60.63, 59.41, 56.47, 52.64, 49.07, 46.08, 37.53, 27.75, 27.02, 23.86. |
| I18 | ¹H NMR (400 MHz, DMSO) δ 8.91-8.87 (m, 2H, Pyridyl-H), 8.16 (d, J = 8.0 Hz, 1H, Pyridyl-H), 7.69 (dd, J = 8.0, 4.8 Hz, 1H, Pyridyl-H), 7.36 (d, J = 0.9 Hz, 2H, Ph-H), 6.49 (d, J = 2.6 Hz, 1H, Ph-H), 3.89 (d, J = 7.4 Hz, 5H, —O—CH₂CH₂CH₂CH₂—N—, Ph-OCH₃), 3.86 (s, 6H, Ph-OCH₃), 3.84 (s, 3H, Ph-OCH₃), 3.74 (s, 3H, Ph-OCH₃), 3.66 (d, J = 11.5 Hz, 2H, Piperidinyl-H), 2.28 (dt, J = 13.4, 9.1 Hz, 5H, —O—CH₂CH₂CH₂CH₂—N—, Piperidinyl-H), 2.02 (s, 3H, N—CH₃), 1.68-1.53 (m, 4H, —O—CH₂CH₂CH₂CH₂—N—), 1.39 (dt, J = 23.0, 11.4 Hz, 4H, Piperidinyl-H). ¹³C NMR (101 NHz, DMSO) δ 172.67, 164.18, 160.71, 158.61, 154.10, 153.10, 151.98, 148.12, 140.42, 139.75, 135.99, 132.76, 126.12, 124.93, 108.90, 106.14, 96.35, 93.52, 72.01, 60.63, 59.21, 56.51, 56.48, 52.68, 45.98, 37.52, 27.76, 27.04, 23.88. |
| I19 | ¹H NMR (400 MHz, DMSO) δ 9.07 (dd, J = 4.2, 1.7 Hz, 1H, Quinolyl-H), 8.53 (dd, J = 8.3, 1.5 Hz, 1H, Quinolyl-H), 8.36 (dd, J = 7.4, 1.3 Hz, 1H, Quinolyl-H), 8.29 (d, J = 8.2 Hz, 1H, Quinolyl-H), 7.76 (t, J = 7.8 Hz, 1H, Quinolyl-H), 7.68 (dd, J = 8.3, 4.2 Hz, 1H, Quinolyl-H), 7.36 (s, 2H, Ph-H), 6.84 (d, J = 1.9 Hz, 1H, Ph-H), 6.48 (s, 1H, Ph-H), 3.90 (s, 5H, —O—CH₂CH₂CH₂—N—, Ph-OCH₃), 3.88 (s, 2H, Piperidinyl-H), 3.85 (s, 6H, Ph-OCH₃), 3.84 (s, 3H, Ph-OCH₃), 3.73 (s, 3H, Ph-OCH₃), 2.69 (t, J = 11.6 Hz, 2H, Piperidinyl-H), 2.32-2.17 (m, 3H, —O—CH₂CH₂CH₂CH₂—N—, Piperidinyl-H), 1.99 (s, 3H, N—CH₃), 1.57 (t, J = 10.7 Hz, 4H, —O—CH₂CH₂CH₂CH₂—N—), 1.41-1.24 (m, 4H, Piperidinyl-H). ¹³C NMR (101 MHz, DMSO) δ 172.66, 164.17, 160.70, 158.60, 153.09, 151.96, 151.77, 143.80, 140.42, 139.74, 137.25, 136.75, 134.35, 132.94, 129.18, 126.21, 126.11, 122.87, 108.89, 106.13, 96.34, 93.52, 72.03, 60.61, 59.92, 56.46, 52.3, 49.06, 46.07, 37.43, 27.86, 27.78, 23.99. |
| I20 | ¹H NMR (400 MHz, DMSO) δ 7.99 (d, J = 7.7, 6.2, 1.5 Hz, 2H, Ph-H), 7.88 (dtd, J = 19.4, 7.5, 1.4 Hz, 2H, Ph-H), 6.84 (d, J = 2.1 Hz, 1H, Ph-H), 3.93 (d, J = 6.4 Hz, 2H, —O—CH₂CH₂CH₂CH₂—N—), 3.90 (s, 3H, Ph-OCH₃), 3.86 (s, 6H, Ph-OCH₃), 3.84 (s, 3H, Ph-OCH₃), 3.74 (s, 3H, Ph-OCH₃), 3.73-3.67 (m, 2H, Piperidinyl-H), 2.75-2.65 (m, 2H, Piperidinyl-H), 2.38 (ddd, J = 11.2, 7.1, 3.1 Hz, 1H, Piperidinyl-H), 2.27 (dd, J = 11.7, 4.5 Hz, 2H, —O—CH₂CH₂CH₂CH₂—N—), 2.04 (s, 3H, N—CH₃), 1.67 (d, J = 11.2 Hz, 2H, —O—CH₂CH₂CH₂CH₂—N—), 1.59 (dd, J = 14.4, 6.7 Hz, 2H, —O—CH₂CH₂CH₂CH₂—N—), 1.45-1.31 (m, 4H, Piperidinyl-H). ¹³C NMR (101 MHz, DMSO) δ 172.68, 164.19, 160.73, 158.62, 153.12, 152.00, 148.33, 140.43, 139.80, 135.17, 132.70, 130.76, 129.94, 126.13, 124.59, 108.92, 106.20, 96.37, 93.55, 72.05, 60.64, 59.26, 56.54, 56.51, 52.78, 45.85, 37.48, 27.81, 27.42, 23.96. |

Embodiment 21 Anti-Plant Bacterial Activity Test of Compounds I1-I20

(1) Test Method

Using turbidimetric method, the inhibitory activity of the target compound on citrus canker pathogen (*Xanthomonas oryzae* pv. *oryzae*), tobacco bacterial wilt pathogen (*Ralstonia solanacearum*) and rice bacterial wilt pathogen (*Xanthomonas axonopodis* pv. *citri*) is tested. The specific operation steps are as follows:

A. 1000 ml of sterilized distilled water is added into a 2000 mL beaker, peptone 5.0 g, yeast powder 1.0 g, glucose 10.0 g, and beef paste 3.0 g are sequentially added under electromagnetic stirring, and the pH value is adjusted to be neutral (7.2±0.2) by sodium hydroxide aqueous solution after the stirring is uniform;

B. After cleaning and sterilizing the test tubes, place them on a test tube rack, use a pipette gun to extract 4.0 mL of the solution prepared in the first step (A) into each test tube, sealed with a silica gel stopper, tied 6 test tubes in a bundle, and sterilize at 121° C. for 20 min for later use;

C. Weighing 0.00375-0.0042 g of the compound to be tested in a centrifuge tube, dissolving with 150 μL of DMSO, transferring 80 μL and 40 μL to the sterilized numbered centrifuge tube respectively, additionally adding 40 μL of DMSO to the centrifuge tube containing 40 μL of sample solution, respectively adding 4 mL of Tween-20 to the centrifuge tube, simultaneously setting thiodiazole copper and bismerthiazol as the positive control reagents and DMSO as a blank control;

D. Extract 1 mL to 3 pieces of solution from each fragmented tube into the test tube in the second step (B) (operate in front of alcohol lamp to prevent other bacteria contamination);

E. Take a blank 96-well plate, measure the blank OD value to exclude the holes with OD value greater than 0.05, then add 200 μL(D) of in-tube solution into each available hole to measure the OD value and record it, finally insert 40 μL of activated citrus canker germ or tobacco bacterial wilt germ or rice bacterial wilt germ into each test tube, wrap the test tube in a newspaper and shake for 24-48 h in a constant temperature shaker at 30° C. and 180 rpm, test the OD value of in-tube solution to track the growth state of bacteria, and take 200 μL of solution in the test tube to measure the OD values and record it after the culture is finished;

F. The formula for calculating the inhibition rate of the compound on bacteria is as follows:

Correction OD=OD value of bacteria-containing medium−OD value of sterile medium $$\text{Inhibition rate (\%)} = \frac{\text{After correction, the bacterial liquid value of blank control medium is } OD - \text{Correction Poison Culture Medium } OD \text{ Value}}{\text{After correction, the bacterial liquid value of blank control medium is } OD} \times 100$$

(2) Results of Bioactivity Test Against Plant Pathogens

TABLE 3

Inhibition Rates a of Compounds I1-I20 against Three Bacteria at Setting Concentrations

| | Inhibition Rate [a]/% | | | | | |
|---|---|---|---|---|---|---|
| | Xac | | Rs | | Xoo | |
| Compound | 100 μg/mL | 50 μg/mL | 100 μg/mL | 50 μg/mL | 100 μg/mL | 50 μg/mL |
| I1 | 99.20 ± 4.48 | 93.55 ± 0.85 | 58.01 ± 6.08 | 47.86 ± 5.55 | 81.34 ± 0.57 | 75.88 ± 1.80 |
| I2 | 99.55 ± 5.61 | 92.76 ± 2.12 | 30.28 ± 8.79 | 34.17 ± 5.87 | 99.01 ± 4.53 | 88.53 ± 5.30 |
| I3 | 94.73 ± 1.63 | 88.81 ± 1.32 | 55.25 ± 2.35 | 56.37 ± 3.41 | 53.31 ± 3.55 | 9.99 ± 7.64 |
| I4 | 81.47 ± 3.58 | 76.83 ± 2.59 | 58.19 ± 8.11 | 46.44 ± 8.48 | 48.16 ± 4.24 | 21.34 ± 3.45 |
| I5 | 95.86 ± 1.19 | 84.37 ± 1.91 | 49.03 ± 5.33 | 18.66 ± 9.95 | 68.42 ± 4.76 | 56.37 ± 2.44 |
| I6 | 99.01 ± 0.64 | 96.13 ± 1.63 | 59.09 ± 4.18 | 26.01 ± 6.89 | 60.99 ± 5.49 | 52.08 ± 6.32 |
| I7 | 92.48 ± 0.65 | 89.57 ± 2.14 | 52.83 ± 6.66 | 50.24 ± 2.21 | 53.46 ± 2.80 | 48.01 ± 3.21 |
| I8 | 88.03 ± 1.19 | 85.13 ± 2.35 | 48.99 ± 2.35 | 47.65 ± 0.35 | 59.94 ± 3.35 | 52.14 ± 3.12 |
| I9 | 42.50 ± 1.87 | 32.80 ± 2.29 | 28.82 ± 3.37 | 12.10 ± 2.57 | 40.25 ± 1.39 | 37.31 ± 5.41 |
| I10 | 45.69 ± 0.50 | 38.60 ± 4.17 | 94.99 ± 1.50 | 57.89 ± 3.30 | 67.71 ± 2.22 | 59.65 ± 2.25 |
| I11 | 54.94 ± 8.29 | 47.25 ± 5.84 | 93.56 ± 0.55 | 46.83 ± 6.39 | 87.57 ± 2.76 | 71.76 ± 4.56 |
| I12 | 35.81 ± 2.40 | 29.56 ± 7.62 | 36.46 ± 7.42 | 45.75 ± 3.32 | 95.44 ± 4.92 | 89.81 ± 1.34 |
| I13 | 48.08 ± 1.17 | 47.25 ± 4.42 | 49.25 ± 4.14 | 43.16 ± 3.98 | 100.00 ± 0.67 | 99.72 ± 1.10 |
| I14 | 73.80 ± 3.68 | 66.18 ± 0.61 | 8.17 ± 3.75 | 20.44 ± 5.03 | 95.49 ± 0.98 | 92.19 ± 0.98 |
| I15 | 67.94 ± 1.42 | 62.21 ± 1.33 | 24.02 ± 2.41 | 3.13 ± 5.57 | 96.11 ± 0.71 | 94.39 ± 0.62 |
| I16 | 74.41 ± 1.31 | 66.33 ± 3.56 | 26.66 ± 4.37 | 27.52 ± 7.50 | 70.41 ± 2.62 | 55.67 ± 6.24 |
| I17 | 99.52 ± 0.87 | 99.00 ± 0.40 | 38.06 ± 1.91 | 45.66 ± 3.26 | 98.29 ± 2.42 | 89.16 ± 1.26 |
| I18 | 93.05 ± 0.55 | 88.69 ± 0.71 | 30.11 ± 1.65 | 46.22 ± 3.27 | 78.12 ± 4.25 | 70.98 ± 3.04 |
| I19 | 89.05 ± 0.47 | 85.44 ± 1.04 | 35.21 ± 6.56 | 37.71 ± 3.71 | 51.83 ± 2.05 | 38.72 ± 1.36 |
| I20 | 97.30 ± 1.97 | 96.57 ± 0.31 | 4.11 ± 3.12 | 21.26 ± 8.58 | 94.47 ± 8.30 | 90.29 ± 4.84 |
| Thiabenone | 70.68 ± 2.47 | 44.97 ± 1.40 | 40.20 ± 3.46 | 20.86 ± 4.42 | 70.12 ± 2.80 | 58.92 ± 8.40 |
| Leaf Blight Azole | 66.63 ± 1.11 | 50.60 ± 1.62 | 65.69 ± 1.63 | 57.63 ± 3.10 | 60.50 ± 3.87 | 39.14 ± 2.18 |

[a]tested three times on average.
[b]took the inhibitory activity of commercial thiodiazole copper and bismerthiazol as the positive controls.

T Using turbidimetric method, the inhibitory activities of the target compounds against citrus canker, tobacco bacterial wilt and rice bacterial wilt are tested with commercial bactericides thiabendazole and fenvalerate as positive controls at the concentration of 100, 50 μg/mL (see Table 3). The test results showed that: All compounds have certain inhibition rates on the tested plant bacteria. Among them, when the concentration is 100 μg/mL, the inhibition rates of compounds I1-8, I14, I16-20 against citrus canker pathogen (Xac) are higher than that of thiodiazole copper (70.68%) and bismerthiazol (66.63%); the inhibition rates of compounds I10 and I11 to tobacco bacterial wilt (Rs) are higher than thiodiazole copper (40.20%) and bismerthiazol (65.69%). Compounds I1-2, I11-18 and I20 all had higher inhibition rates against *Xanthomonas oryzae* (Xoo) than thiodiazole copper (70.12%) and bismerthiazol (60.50%). When the concentration is 50 μg/mL, the inhibition rates of compounds I1-8 and I14-20 against citrus ulcer bacteria (Xac) is higher than that of thiodiazole copper (44.97%) and bismerthiazol (50.60%). The inhibition rate of compound I10 against tobacco bacterial wilt (Rs) is close to that of bismerthiazol (57.63%). The inhibition rates of I1-2, I10-15, I17-18 and I20 against Xoo are higher than that of thiodiazole copper (58.92%) and bismerthiazol (39.14%). The above experimental activity data showed that sulfonamide-containing 4-(N-methyl) amino piperidine myricetin derivatives has certain inhibitory effect on plant pathogens (citrus ulcer bacteria, tobacco *Solanacearum*, rice blight pathogen), and parts of the target compounds with good inhibitory activities on plant pathogens performance can be used as potential inhibition of plant pathogen drugs, which has a good application prospects.

In summary, it is only a preferred embodiment of the present invention and is not intended to limit the present invention in any form. Any simple modifications, equivalent changes and modifications made to the above embodiments according to the technical essence of the present invention without departing from the technical scheme of the present invention are still within the scope of the technical scheme of the present invention.

What is claimed is:

1. A method of preparing 4-(N-methyl) aminopiperidine myricetin derivatives containing sulfonamide, the synthetic route of which is as follows: mixing myricetin with potassium carbonate (K2CO3) and N,N-dimethylformamide (DMF) and adding with methyl iodide (CH3I) to perform reaction, and followed by adding absolute ethyl alcohol (CH3CH2OH) to heat to reflux to obtain a clarified solution and adding concentrated hydrochloric acid (HCl) into the clarified solution under reflux, thereby (1) obtaining 3-Hydroxy-3',4',5',5,7-pentamethoxy myricetin (intermediate a)

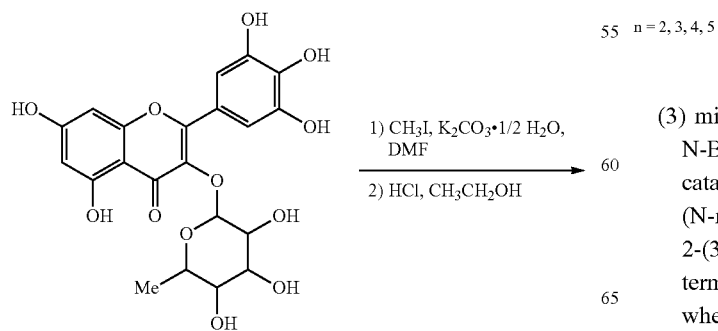

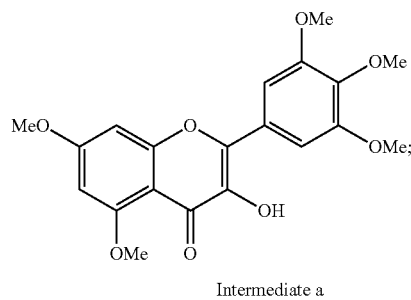

Intermediate a (2) combining the intermediate a with dibromoalkanes (Br(CH$_2$)$_n$Br) and potassium carbonate as a catalyst and DMF as a solvent for 1 day (d) at room temperature (rt) to obtain 3-bromo-5,7-dimethoxy-2-(3,4,5-trimethoxyphenyl)-4H-chromene-4-one (intermediate b):

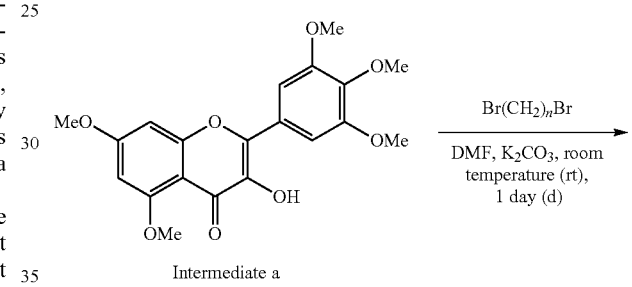

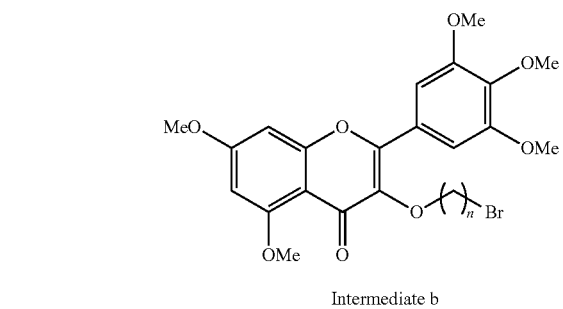

Intermediate b n = 2, 3, 4, 5

(3) mixing the intermediate b and 4-(N-methyl) amino-N-Boc piperidine by taking potassium carbonate as a catalyst and acetonitrile as a solvent to prepare 3-(4-(N-methyl) amino-N-Boc piperidine)-5,7-dimethoxy-2-(3,4,5-trimethoxyphenyl)-4H-chromene-4-one (intermediate c) under reflux and stirring at 80° C., wherein the Boc of intermediate c is a tert-butylcarbonyl protecting group:

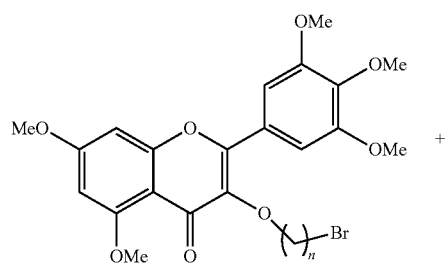

Intermediate b

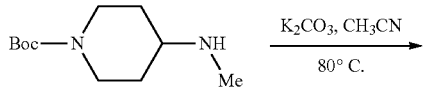

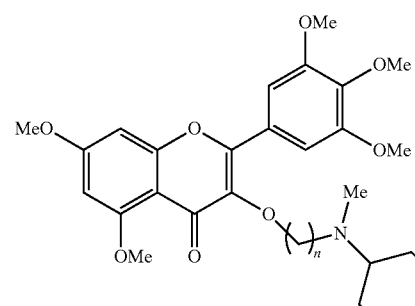

Intermediate c n = 2, 3, 4, 5

(4) removing the tert-butylcarbonyl (Boc) protecting group from the intermediate c with methanol (CH3OH) as a solvent and hydrochloride (HCl) at room temp (rt) for 2 hours (2h) to obtain hydrochloride (intermediate d) of the 3-(4-(N-methyl) aminopiperidine)-5,7-dimethoxy-2-(3,4,5-trimethoxyphenyl)-4H-chromene-4-one

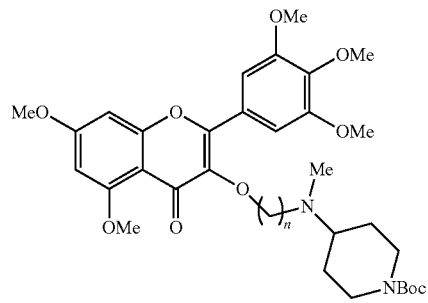

Intermediate c

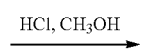

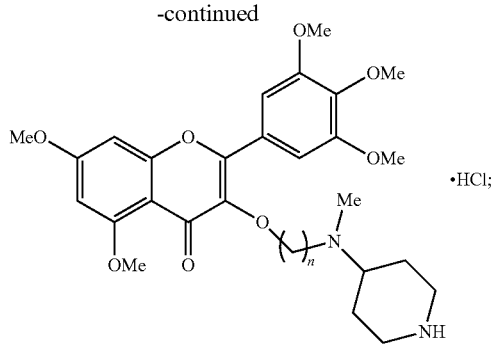

Intermediate d n = 2, 3, 4, 5

(5) mixing the intermediate d and substituted sulfonyl chloride by taking potassium carbonate as a catalyst and absolute ethyl alcohol as a solvent to prepare the 4-(N-methyl) aminopiperidine myricetin derivatives containing sulfonamides (target compound I)

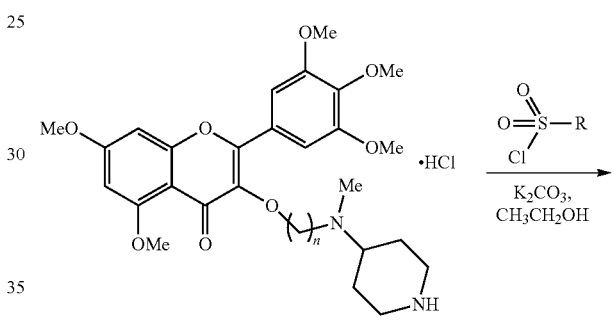

Intermediate d

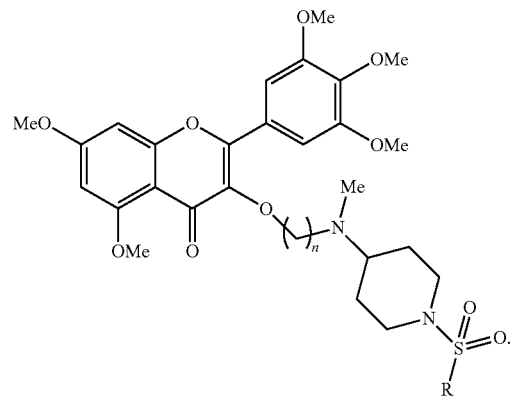

target compound I n = 2, 3, 4, 5

* * * * *